(12) United States Patent
Hsieh et al.

(10) Patent No.: US 9,161,729 B2
(45) Date of Patent: Oct. 20, 2015

(54) APPARATUS FOR X-RAY PHOTOGRAPHY

(71) Applicant: INSTITUTE OF NUCLEAR ENERGY RESEARCH ATOMIC ENERGY COUNCIL, EXECUTIVE YUAN, Taoyuan County (TW)

(72) Inventors: Ho-Hui Hsieh, Taoyuan County (TW); Meei-Ling Jan, Taoyuan County (TW); Tien-Hsiu Tsai, Taoyuan County (TW)

(73) Assignee: INSTITUTE OF NUCLEAR ENERGY RESEARCH ATOMIC ENERGY COUNCIL, EXECUTIVE YUAN, Taoyuan County (TW)

( * ) Notice: Subject to any disclaimer, the term of this patent is extended or adjusted under 35 U.S.C. 154(b) by 199 days.

(21) Appl. No.: 13/965,381

(22) Filed: Aug. 13, 2013

(65) Prior Publication Data

US 2014/0140478 A1     May 22, 2014

(30) Foreign Application Priority Data

Nov. 20, 2012    (TW) ............................. 101143280 A

(51) Int. Cl.
   *A61B 6/14*      (2006.01)
   *A61B 6/06*      (2006.01)
   *B60K 7/00*      (2006.01)

(52) U.S. Cl.
   CPC ... *A61B 6/14* (2013.01); *A61B 6/06* (2013.01); *B60K 7/0007* (2013.01)

(58) Field of Classification Search
   CPC ............ A61B 6/06; A61B 6/14; A61B 6/032; B60K 7/0007; G21K 1/02
   USPC ........... 378/21, 38, 39, 40, 62, 145, 147, 156, 378/160, 168
   See application file for complete search history.

(56) References Cited

U.S. PATENT DOCUMENTS

| | | | |
|---|---|---|---|
| 2003/0002626 A1* | 1/2003 | Hoheisel et al. | 378/98.8 |
| 2004/0197727 A1* | 10/2004 | Sachdeva et al. | 433/24 |
| 2009/0225932 A1* | 9/2009 | Zhu | A61B 6/032 378/7 |
| 2011/0122993 A1* | 5/2011 | Ichizawa | 378/51 |

OTHER PUBLICATIONS

Som et al., A Painless Retroauricular Mass in a Patient with Myotonic Dystrophy: Computed Tomographic Documentation of the Bone Changes that Occur in the Skull Base, 1997, Skull Base Surgery, vol. 7, No. 4, p. 224.*
Pasler et al., Pocket atlas of dental radiology, Sep. 2007, Thieme New York, p. 85, 86.*

* cited by examiner

*Primary Examiner* — Irakli Kiknadze
*Assistant Examiner* — Julio M Duarte-Carvajalino
(74) *Attorney, Agent, or Firm* — WPAT, PC; Justin King

(57) ABSTRACT

An apparatus for X-ray photography includes a first X-ray source, a first driving device, and an image detecting device. The first X-ray source has a light emitting end, provided with a block element. The first X-ray source generates an X-ray beam, and the block element is used for constraining a projection field of the X-ray beam, so that the X-ray beam has a first boundary. The X-ray beam is cast onto an object, and the object has a reference center and an imageable area. The first driving device is used for driving the first X-ray source to rotate around the object within an angle range with the reference center of the object as a center, so that when the first X-ray source is located at a first position, the first boundary passes through the reference center.

6 Claims, 5 Drawing Sheets

APPARATUS FOR X-RAY PHOTOGRAPHY

BACKGROUND OF THE INVENTION

1. Field of Invention

The present invention relates to an apparatus for X-ray photography, and in particular, to an apparatus for X-ray photography that can keep an X-ray beam away from a non-imageable area in a photographing process.

2. Related Art

Extraoral dental X-ray radiography, such as two-dimensional dental panoprex and three-dimensional computed tomography (CT), is often used for radiographing teeth, the jaw and facial bones, and peripheral soft tissues, and is a useful tool in dental diagnosis and auxiliary treatment.

An X-ray photographical contrast mainly results from penetration attenuation caused by components, density and thickness of a matter penetrated by an X-ray, and most photon energy lost in the penetration process is absorbed by human tissues and is converted into a radiation dose. Referring to FIG. 1, targets of dental X-ray radiography are mainly located below the cranium base of the skull 10 and in a range of the oral cavity and the jaw and facial bones in front of the external acoustic meatus (EAM). In skull morphology, the petrous pyramid and the midsagittal plane are boundaries of the shape of the cranium base, and a symmetrical pyramid structure with the sella turcica 11 as a vertex and having left and right angles of 47 degrees is a non-imageable area. In other words, an actual range required in dental X-ray radiography includes an area in the cranium base with the petrous pyramid and the midsagittal plane as boundaries and the sella turcica 11 as a vertex and having left and right angles of 133 degrees and a round cake column range having a height from the infraorbitomeatal line (IOML) of the skull to the mandible base. However, in a conventional disadvantageous extraoral X-ray scanning mode in the prior art, for example, dental panoprex scanning and dental CT scanning, to implement X-ray dental panoprex imaging or to obtain information of X-ray projection with an enough angle to reconstruct a three-dimensional image, most extraoral dental X-ray image systems adopt a mode of synchronized center rotation scanning in which an X-ray source and an image detecting device rotate about a center at an angle of 180 degrees for scanning.

However, since the oral cavity is located at a front and bottom position of the head and neck portion and an X-ray has a characteristic of forward advancing along a straight line, during the synchronized center rotation scanning, a non-imageable head and neck area (that is, the non-imageable area formed by a symmetrical pyramid structure area with the sella turcica 11 as the vertex and having left and right angles of 47 degrees) is often unavoidably and directly exposed to an X-ray scanning beam, resulting in extra X-ray penetration attenuation, so that the X-ray source needs a higher power to output a radiation amount sufficient for an image receiving apparatus to form an image; meanwhile, a radiation dose received by the human body is increased. If the synchronized center rotation scanning avoids scanning the non-dental imageable area such as the head and neck portion, sufficient X-ray projection image information cannot be obtained, so that a complete dental X-ray image cannot be formed.

SUMMARY OF THE INVENTION

In view of the disadvantages of the prior art, the present invention provides an apparatus for X-ray photography, which can keep an X-ray beam away from a non-imageable area in a photographing process in a scanning mode of asymmetric rotation of an X-ray source and an image detecting device.

When being applied in dental radiography, this apparatus for X-ray photography has characteristics of a scanning mode of bilateral three-dimensional partial center rotation within a limited angle, and a dental scanning range of humans is divided into a left half part and a right half part according to the bone anatomical structure of the human body. A dental radiographing range is scanned in such a manner that a detecting device is oriented toward a center in a fixed manner and an X-ray emitting source rotates about the center of a circle and radiates light, and an X-ray block element is used for shaping a conical X-ray beam irradiating field, so that an edge tangent of the irradiating field is kept away from non-dental X-ray radiographing tissues such as the skull and the neck portion, and enters an X-ray penetration range. In this way, the X-ray scanning covers the full dental scanning range of the full oral cavity with minimum penetration attenuation. If only a small range of extraoral X-ray radiographing of a single side needs to be performed, by radiographing a half of an imageable range and reducing the rotation angle of the X-ray emitting source, the angle distribution of the X-ray irradiating field is just enabled to meet an imaging demand.

In an embodiment, the present invention provides an apparatus for X-ray photography, which includes an X-ray source, a first driving device, and an image detecting device. The X-ray source has a light emitting end, the light emitting end is provided with a block element. The X-ray source generates an X-ray beam through the light emitting end, and the block element is used for constraining a projection field of the X-ray beam, so that the X-ray beam has a first boundary. The X-ray beam is cast onto an object, and the object has a reference center and an imageable area. The first driving device is used for driving the X-ray source to rotate around the object within an angle range with the reference center of the object as a center. In the rotation process of the X-ray source, the X-ray beam is projected onto the imageable area, and when the X-ray source is located at a first position, the first boundary passes through the reference center. The image detecting device is disposed at a side of the object and faces the X-ray source. After being cast onto the object, the X-ray beam is projected onto the image detecting device, thereby forming an image on the image detecting device.

In order to make the structures, objectives, and efficacies of the present invention comprehensible to the examiner, the present invention is illustrated in detail below with reference to the accompanying drawings.

BRIEF DESCRIPTION OF THE DRAWINGS

The present invention will become more fully understood from the detailed description given herein below for illustration only, and thus are not limitative of the present invention, and wherein.

DETAILED DESCRIPTION OF THE INVENTION

Technical means and efficacies used by the present invention to achieve the objectives are described below with reference to the accompanying drawings, the embodiments with the accompanying drawings are merely provided for auxiliary illustration, so as to facilitate comprehension of the examiner. However, the technical means of this application is not limited by the listed drawings.

Figure 1:
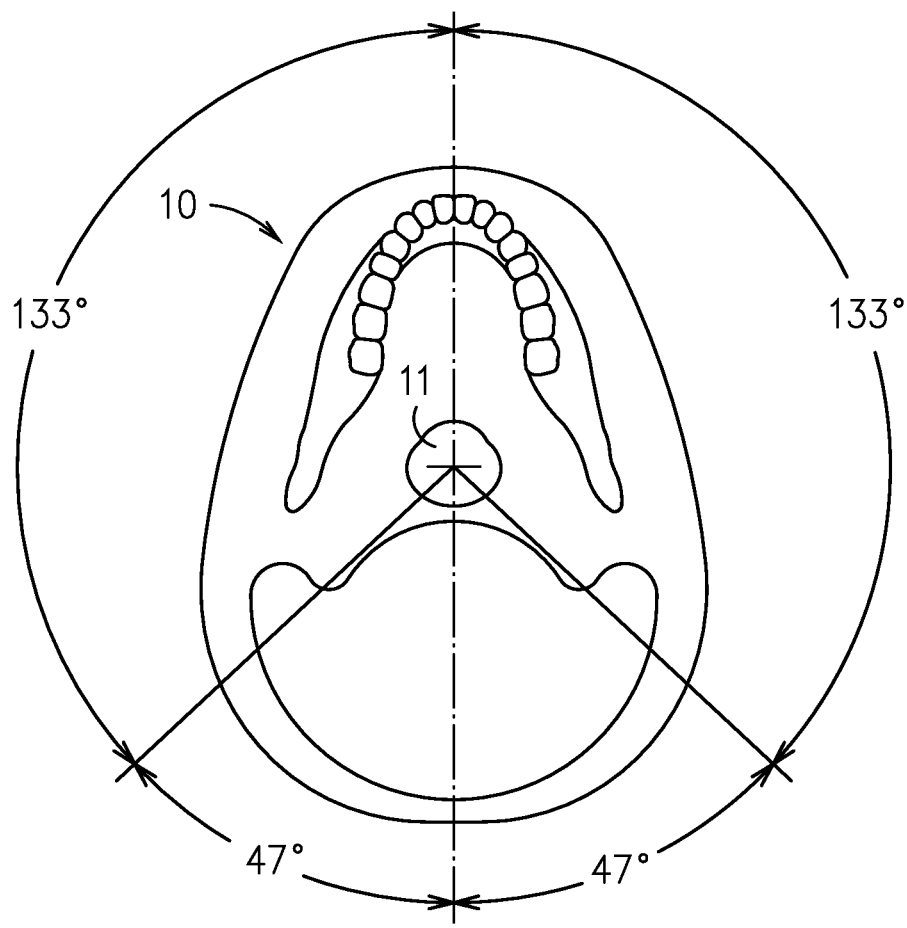
FIG. 1 is a schematic view of an imageable area and a non-imageable area in X-ray photographing in the prior art.
Figure 2A:
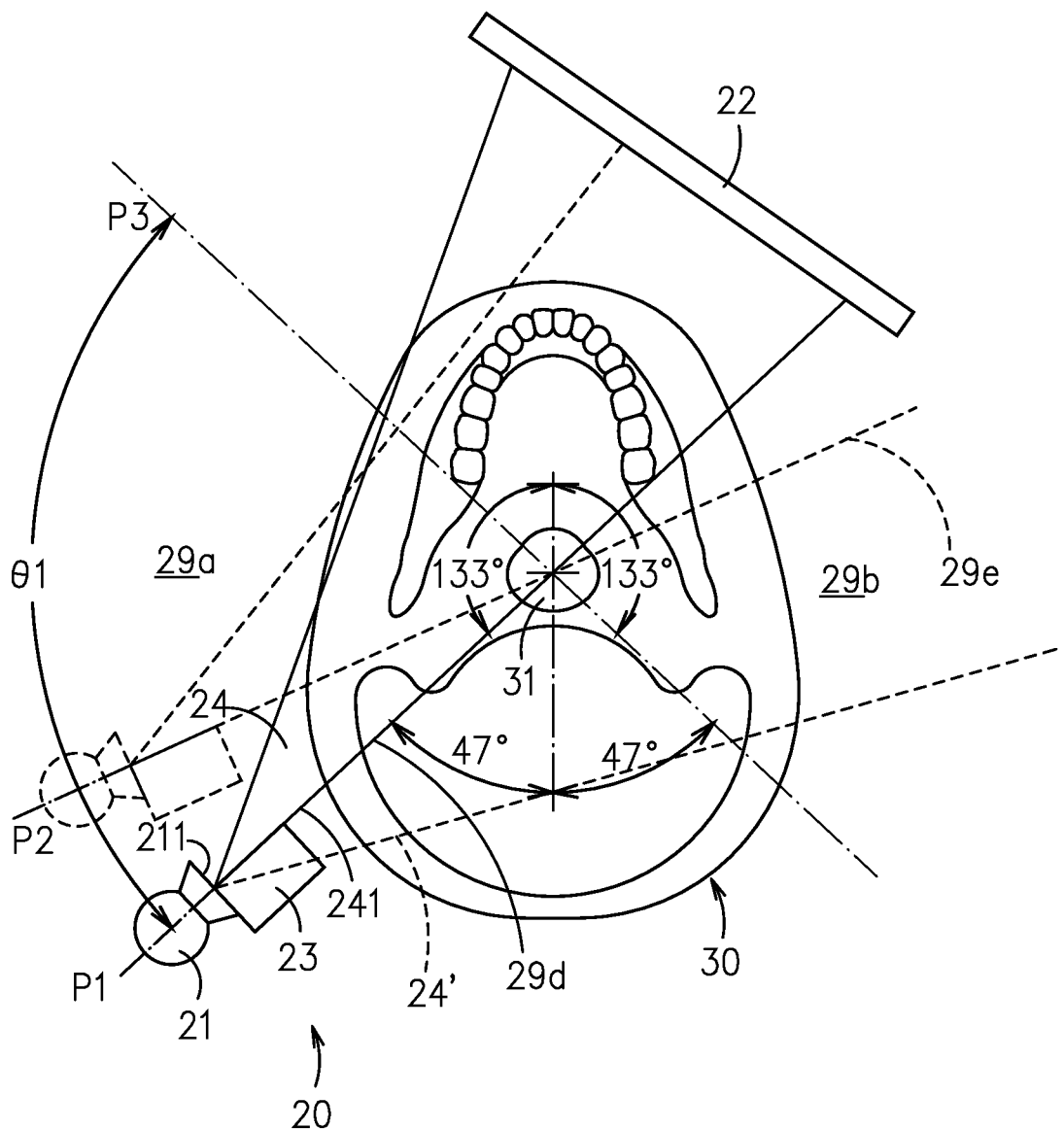
FIG. 2A to FIG. 2B are schematic structural views of Embodiment 1 of the present invention.
Figure 2B:
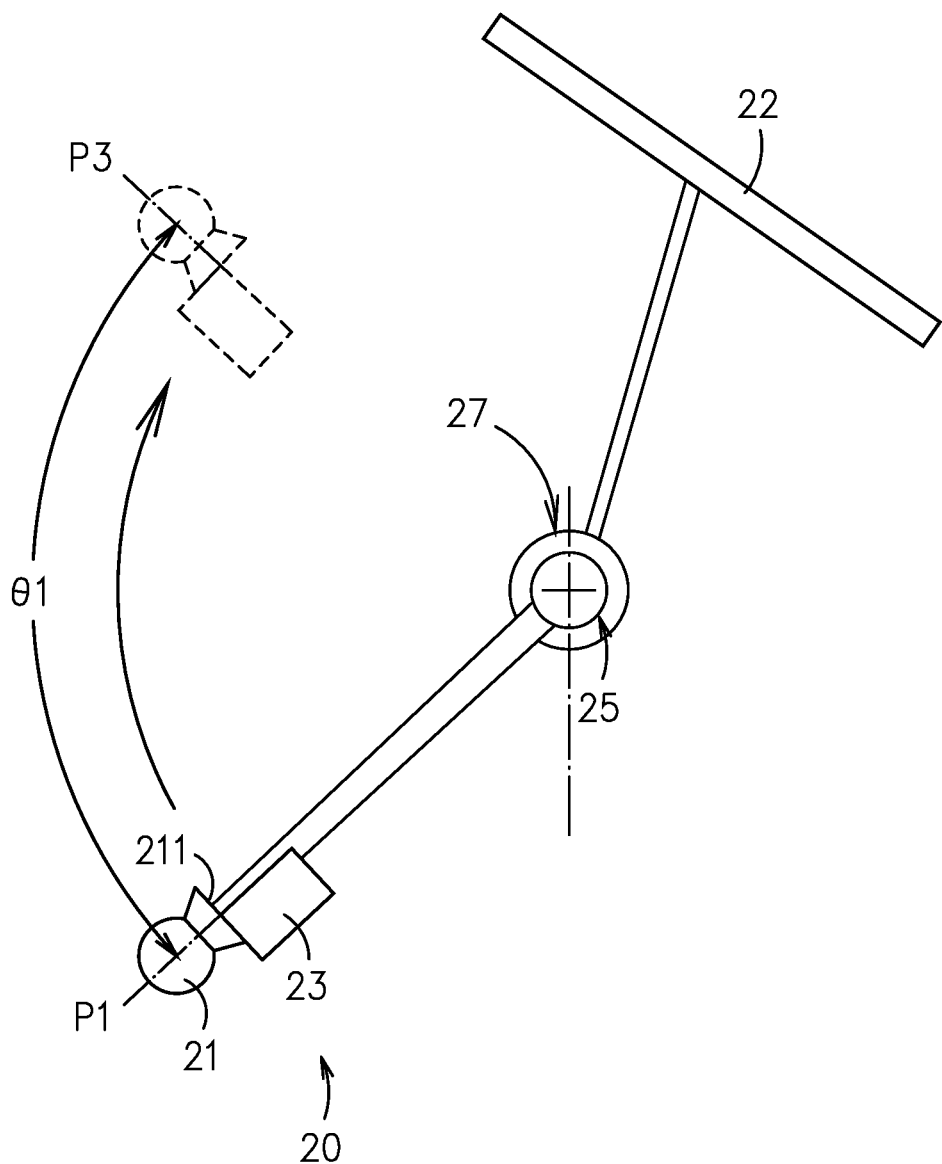

Referring to the embodiment shown in FIG. 2A and FIG. 2B, an apparatus for X-ray photography 20 includes an X-ray source 21 and an image detecting device 22. The X-ray source 21 is disposed at one side of an object 30, and the image detecting device 22 is disposed at the other side of the object 30 and faces the X-ray source 21.

The X-ray source 21 has a light emitting end 211, and the light emitting end 211 is provided with a block element 23. The X-ray source 21 generates X-ray beams 24 and 24' through the light emitting end 211. The block element 23 is used for constraining projection field of the X-ray beams 24 and 24', so that the X-ray beam has a first boundary 241. In this embodiment, the block element 23 is a shield block, made of a material capable of blocking radioactive rays, for example, but not limited to, a lead block or a cement block. Through shielding provided by the block element 23, the beam 24' is shielded, so that only the beam 24 of the beams generated by the X-ray source 21 is left. In this embodiment, the first boundary 241 can be considered as a central line of the beams 24 and 24'. The X-ray beam 24 is cast onto the object 30, and the object 30 is the skull of a human body. The object 30 has imageable areas 29a and 29b, and the imageable areas 29a and 29b are located below the cranium base and in a range of the oral cavity and the jaw and facial bones in front of an EAM. The imageable areas are an area (a fan-shaped area with an entire angle of 266 degrees) in the cranium base with the petrous pyramid and the midsagittal plane as boundaries and the sella turcica 31 as a vertex and having left and right angles of 133 degrees and a round cake column range having a height from the IOML of the skull to the mandible base. A symmetrical pyramid structure formed with the petrous pyramid and the midsagittal plane as boundaries and the sella turcica 31 as a vertex and having left and right angles of 47 degrees is a non-imageable area (a fan-shaped area of an entire angle of 94 degrees). A center of the sella turcica 31 serves as a reference center of the object 30.

The X-ray source 21 is connected to a first driving device 25, and the first driving device 25 is used for driving the X-ray source 21 to rotate, with the reference center of the object 30 (that is, the center of the sella turcica 31) as a center, around the object 30 within a range of an angle θ1 from a first position P1 to a second position P2. In this embodiment, the first driving device 25 is a rotation module, for example, a combination of a motor and a rotation arm. The rotation arm is connected to the X-ray source 21, and by means of a rotating force of the rotation module, the rotation arm is driven to rotate, thereby driving the X-ray source 21 to rotate. It should be noted that the first driving device 25 is not limited to the driving device shown in FIG. 2B, and persons of ordinary skill in the art can implement the first driving device 25 in different manners according to the prior art. For example, in another embodiment, by means of a curved rail, the X-ray source 21 rotates, with the reference center of the object 30 (that is, the center of the sella turcica 31) as a center, around the object 30 in a range of an angle θ1 from the first position P1 to the second position P2. The image detecting device 22 is connected to a second driving device 27, and the second driving device is used for driving the image detecting device 22 to present an asymmetric scanning mode with the X-ray source 21. In the asymmetric scanning mode, the image detecting device 22 and the X-ray source 21 are rotated in an asynchronous manner, so that the image detecting device 22 and the X-ray source 21 are kept at positions where the X-ray beam 24 passing through the object 30 can be received. In an embodiment, the second driving device 27 is a rotation module, for example, a combination of a motor and a rotation arm. The rotation arm is connected to the image detecting device 22, and by means of a rotating force of the rotation module, the rotation arm is driven to rotate, thereby driving the image detecting device 22 to rotate. It should be noted that the image detecting device 22 is not rotated synchronously with the X-ray source 21 but is rotated at an asynchronous rotation angle to a position where the beam passing through the object 30 can be received. In an embodiment, when no beam is generated, the image detecting device 22 is first rotated to a fixed position, and then the X-ray source 21 is enabled to generate an X-ray beam, and the X-ray beam is cast onto the object by means of rotation. Therefore, in the embodiments of the present invention, when the X-ray source 21 is rotating, the image detecting device 22 is kept fixed.

As shown in FIG. 2A, when the X-ray source 21 is located at the first position P1, the first boundary 241 is directly used as a bottom boundary 29d of the left 133-degree area with the sella turcica 31 as a vertex in the imageable areas 29a and 29b. In a process that the X-ray source 21 is driven to rotate from the P1 in the range of the angle θ1, the first boundary 241 is rotated with the center of the sella turcica 31 as a center. Therefore, in the rotation process of the X-ray source 21, the X-ray beam 24 is always projected onto the imageable area, and will not be projected onto the non-imageable area. When the X-ray source 21 is located at the second position P2, the first boundary 241 is directly used as a bottom boundary 29e of a right 133-degree area with the sella turcica 31 as a vertex in the imageable areas 29a and 29b. After being cast onto the object 30, the X-ray beam 24 is then projected onto the image detecting device 22, so that an image can be formed on the image detecting device 22. It should be noted that a third position P3 is a rotation limit of the X-ray source 21. However, in actual implementation, the X-ray source 24 is not necessarily rotated to the limit position P3. Since a general X-ray beam has a symmetrical X-ray irradiating filed without shielding provided by the block element 23, in this embodiment, by means of shielding provided by the block element 23, the irradiating field of the X-ray beam becomes an asymmetric irradiating filed, and the first boundary 241 at a side becomes a boundary of the imageable area when the X-ray source 21 is rotated to the first and second positions.

Figure 3:
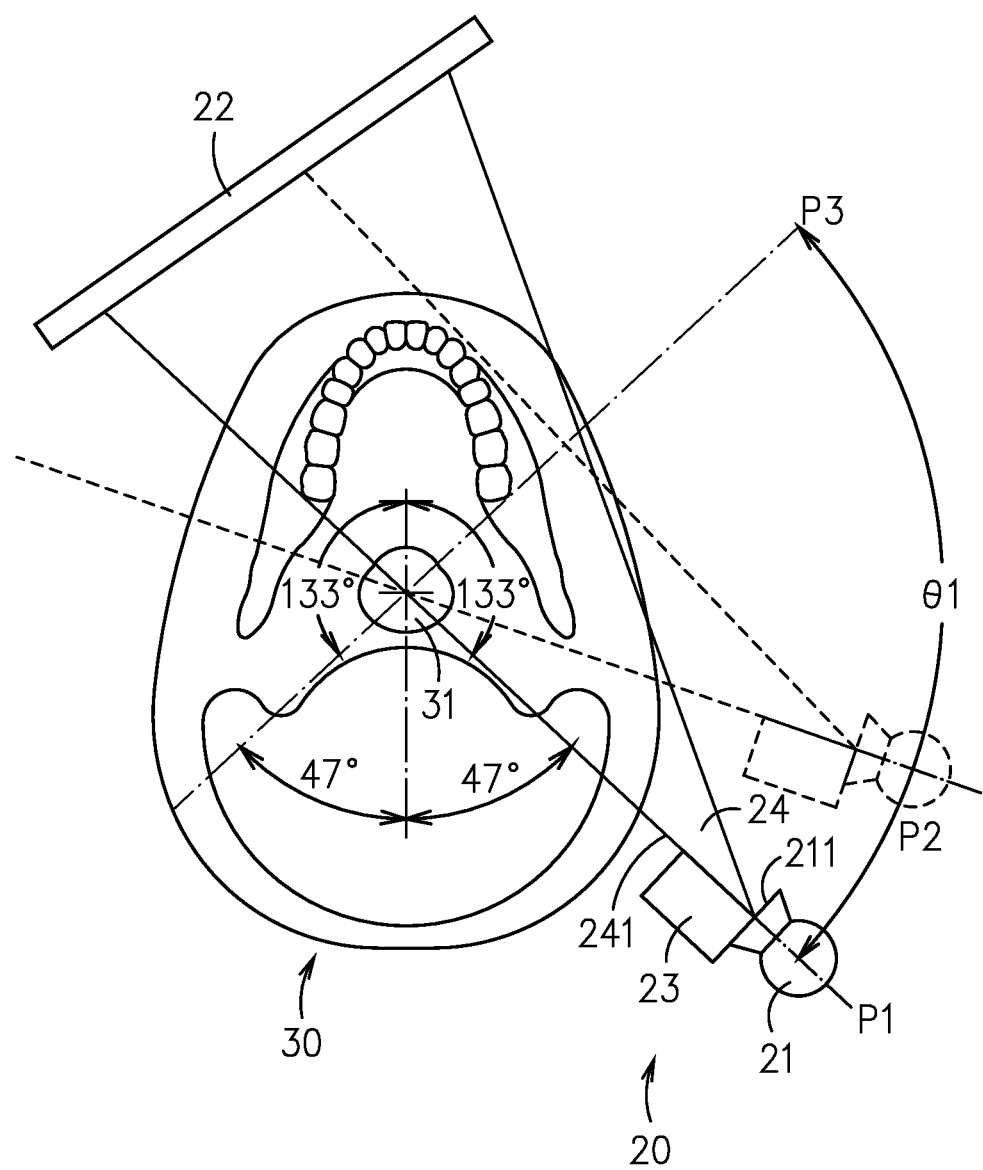
FIG. 3 is a schematic view of another side of a scanned object.
Figures 4, 4A, 4B:
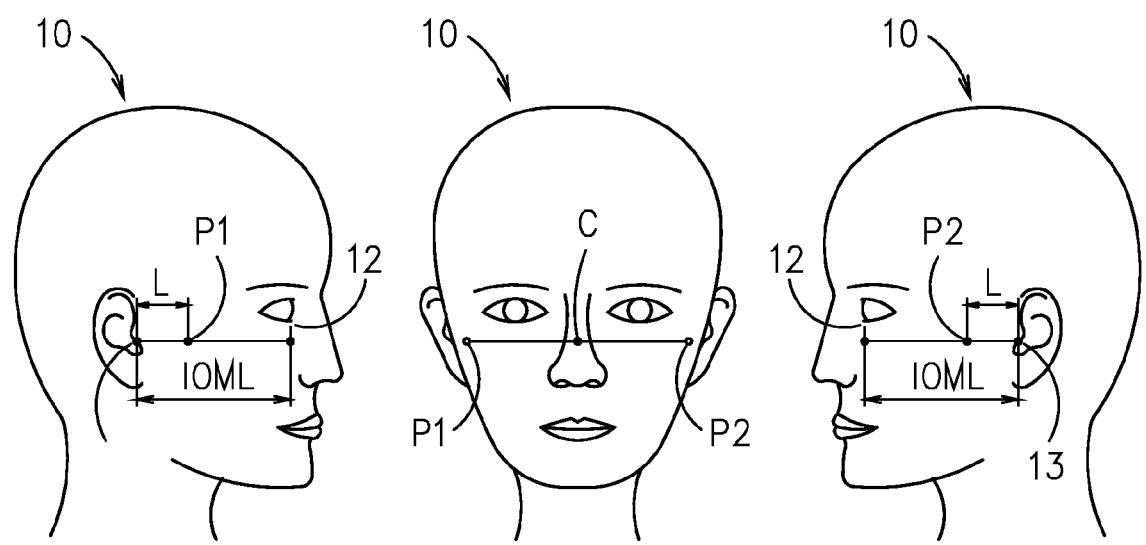
FIG. 4, FIG. 4A and FIG. 4B are schematic views showing defining of a reference central point in the present invention.

Referring to an embodiment shown in FIG. 3, a structure of the embodiment is symmetrical to a structure of the embodiment shown in FIG. 2A. For the embodiment shown in FIG. 2A, the apparatus for X-ray photography 20 in FIG. 2A is mainly used for scanning a left image of the object 30, and the apparatus for X-ray photography 20 in FIG. 4 is mainly used for scanning a right image of the object 30. A user may set the apparatus for X-ray photography 20 on one side of the object 30, and then controls the apparatus for X-ray photography 20 to move from one side of the object 30 to the other side of the object 30, provided that the X-ray beam 24 is controlled to be away from the non-imageable area in the movement process. The manner of moving the X-ray source on the other side can be obtained with reference to the content corresponding to the FIG. 2A and FIG. 2B.

Referring to FIG. 4, FIG. 4A and FIG. 4B, a method for defining a reference central axis of X-ray rotational scanning is illustrated. FIG. 4 is a front view of the skull 10, and FIG. 4A and FIG. 4B are respectively a right view and a left view of the skull 10.

First, as shown in FIG. 4A and FIG. 4B, IOMLs on the left and right sides of the skull 10 are respectively located, and the IOML is a distance from the lower eye socket 12 to the EAM 13 of the skull 10. Next, surface reference points C1 and C2 are defined at positions with a length L from the EAM 13 on the left and right IOMLs, and the length L is located within a range of ¼ o ⅓ of the IOML. For example, if the IOML is 9.6 centimeters, lengths of distances from the surface reference points C1 and C2 to the EAM are about 2.4 to 3.2 centimeters. Preferably, the surface reference points C1 and C2 on the two sides of the skull 10 are symmetrical to each other. After that, an intersection point of a line linking the surface reference points C1 and C2 and a central sagittal section of the skull is used as a central axis reference point C, as shown in FIG. 4. It should be emphasized that the central axis reference point C is located inside the skull 10, and when X-ray radiographical scanning is actually performed on a subject, the IOML of the head of the subject is parallel to the ground when the subject is in a standing or sitting state, and an axial line passing through the central axis reference point C and being perpendicular to the ground is defined as the reference central axis of the X-ray rotational scanning. When the subject is in a flat-lying state, the IOML of the head is perpendicular to a bed surface contacted by the head, and an axial line passing through the central axis reference point C and being parallel to the bed surface and a head-to-foot direction of a flat-lying human body is defined as a reference central axis of the X-ray rotational scanning.

Therefore, the subject may be in the standing state, the head of the subject is placed in an X-ray radiographing range, the IOML of the head is parallel to the ground, and the central sagittal section of the skull is tangent to a 180-degree angle position of the X-ray scanning. The subject occludes teeth, and an occlusal surface is at a height approximately corresponding to a central horizontal line of a light sensing area of the detecting device, and an axial line passing through the central axis reference point C and being perpendicular to the ground is defined as the reference central axis of the X-ray rotational scanning.

To sum up, in the apparatus for X-ray photography according to the present invention, since the X-ray beam can be kept away from non-dental X-ray radiographing tissues such as the skull bone and the neck portion, direct exposure of a human body to the X-ray scanning beam can be avoided, and extra X-ray penetration attenuation can be reduced, so that the X-ray source can use a low power to output a radiation dose sufficient for an image receiving device to form an image, and meanwhile, the radiation dose received by the human body is decreased. If extraoral X-ray radiographing only needs to be performed at a single side in a small range, by radiographing a half of the imageable range and reducing the rotation angle of the X-ray source, the angle distribution of the X-ray irradiating field is just enabled to meet an imaging demand.

The above description is only the embodiments of the present invention, and should not be construed as limitations to the implementation scope of the present invention. Equivalent variations and modifications made according to the appended claims of the present invention shall fall within the protection scope of the present invention. We will be appreciated if the examiner conducts careful examination and grant the present application a patent right.

What is claimed is:

1. An apparatus for X-ray photography, comprising:
a first X-ray source, having a light emitting end, wherein the light emitting end is provided with a block element, the first X-ray source generates an X-ray beam through the light emitting end, the block element is used for constraining a projection field of the X-ray beam, so that the X-ray beam has a first boundary at a central line of said projection field intersecting a sella turcica of an object, an anterior half of said X-ray beam is cast onto said object, the object has a reference center and an imageable area, and the block element is a shield block for shielding a posterior half of said X-ray beam posterior to said first boundary;
a first driving device, used for driving the first X-ray source to rotate around the object within an angle range with the reference center of the object as a center, wherein, in the rotation process of the first X-ray source, the X-ray beam is projected onto the imageable area, and when the first X-ray source is located at a first position, the first boundary is a boundary of the imageable area; and
an image detecting device, disposed at a side of the object and facing the first X-ray source, wherein after being cast onto the object, the X-ray beam is projected onto the image detecting device, thereby forming an image on the image detecting device.

2. The apparatus for X-ray photography according to claim 1, wherein the image detecting device is connected to a second driving device, the second driving device is used for driving the image detecting device to rotate about said reference center, and said image detecting device and said first X-ray source are rotated in an asynchronous manner.

3. The apparatus for X-ray photography according to claim 1, wherein, in the rotation process of the first X-ray source, the first boundary rotates with the reference center as a center.

4. The apparatus for X-ray photography according to claim 1, wherein the object is the skull of a human body, and the imageable area is located below the cranium base and in a range of the oral cavity and the jaw and facial bones in front of the external acoustic meatus (EAM).

5. The apparatus for X-ray photography according to claim 4, wherein the imageable area is an area in the cranium base with the petrous pyramid and the midsagittal plane as boundaries and the sella turcica as a vertex and having left and right angles of 133 degrees and a round cake column range having a height from the infraorbitomeatal line (IOML) of the skull to the mandible base.

6. The apparatus for X-ray photography according to claim 1, further comprising a collimator, for constraining a projection field of the X-ray beam passing through the block element.

* * * * *